(12) United States Patent  
Hunt

(10) Patent No.: US 8,644,914 B2  
(45) Date of Patent: Feb. 4, 2014

(54) METHODS OF MEASUREMENT OF DRUG INDUCED CHANGES IN CARDIAC ION CHANNEL FUNCTION AND ASSOCIATED APPARATUS

(75) Inventor: Anthony Charles Hunt, Glasgow Strathclyde (GB)

(73) Assignee: Cardio-Qt Limited, Hillington (GB)

( * ) Notice: Subject to any disclaimer, the term of this patent is extended or adjusted under 35 U.S.C. 154(b) by 1080 days.

(21) Appl. No.: 12/663,476

(22) PCT Filed: Jun. 6, 2008

(86) PCT No.: PCT/GB2008/050418  
§ 371 (c)(1),  
(2), (4) Date: Dec. 7, 2009

(87) PCT Pub. No.: WO2008/149159  
PCT Pub. Date: Dec. 11, 2008

(65) Prior Publication Data  
US 2010/0179447 A1   Jul. 15, 2010

(30) Foreign Application Priority Data  
Jun. 8, 2007   (GB) .................................. 0710963.0

(51) Int. Cl.  
*A61B 5/0402* (2006.01)  
*A61B 5/0452* (2006.01)

(52) U.S. Cl.  
CPC ........... *A61B 5/04028* (2013.01); *A61B 5/0452* (2013.01)  
USPC ........................................................ 600/509

(58) Field of Classification Search  
USPC .......................... 600/509, 512–513, 519, 521  
See application file for complete search history.

(56) References Cited

U.S. PATENT DOCUMENTS

| | | | |
|---|---|---|---|
| 5,483,968 A | 1/1996 | Adam et al. | |
| 2002/0128565 A1* | 9/2002 | Rudy | 600/509 |
| 2003/0018277 A1 | 1/2003 | He | |

FOREIGN PATENT DOCUMENTS

| | | |
|---|---|---|
| WO | WO 99/05962 A1 | 2/1999 |
| WO | WO 2007/013994 A2 | 2/2007 |

OTHER PUBLICATIONS

International Search Report for International Application No. PCT/GB2008/050418 (Oct. 8, 2008).

(Continued)

*Primary Examiner* — Carl H Layno  
*Assistant Examiner* — Jessica Sarcione  
(74) *Attorney, Agent, or Firm* — Jenkins, Wilson, Taylor & Hunt, P.A.

(57) ABSTRACT

This invention relates to the healthcare industry and to a novel non-invasive body surface bipolar ECG to monitor the action potential (AP) of the myocardium muscle. The invention uses surface ECG signals to deduce information on the cardiac ion channels, founded on the reconstruction of the epicardial ECG T-wave using a single transfer filter function of the frequency domain. Ion channels conductances obtained are then used to calculate action potential EndAP, EpiAP and MAP of the myocardium. These APs values can in turn be used to calculate post drug transmural dispersion of repolarisation values to giving an indication of possible cardiac arrhythmias. The invention further relates to various apparatus for carrying out the invention, including an array of bipolar electrodes which in use is arranged on the body surface so as to comprise multiples of orthogonally bisecting electrodes.

24 Claims, 5 Drawing Sheets

(56) References Cited

OTHER PUBLICATIONS

UK Intellectual Property Office—Search and Advisory Service. Search Report for PSI Heartsignals Global Limited, Subject of Search: an ECG arrangement wherein body surface ECG signals are converted to epicardial signals by way of an "inverse model", the arrangement being used to monitor the effect of drugs on the heart. (Oct. 16, 2007).

Ghanem et al., "Imaging Dispersion of Myocardial Repolarization, II: Noninvasive Reconstruction of Epicardial Measures," Circulation, vol. 104, pp. 1306-1312 (2001).

Ramanathan et al., "Noninvasive electrocardiographic imaging for cardiac electrophysiology and arrhythmia," Nature Medicine, vol. 10, No. 4, pp. 422-428 (Apr. 2004).

Smith et al., "The Forward and Inverse Problems: What Are They, Why Are They Important, and Where Do We Stand?," Journal of Cardiovascular Electrophysiology, vol. 12, No. 2, pp. 253-255 (Feb. 2001).

Antzelevitch, "Role of transmural dispersion of repolarization in the genesis of drug-induced torsades de pointes," Heart Rhythm, Elsevier, vol. 2, No. 11, pp. S9-S15 (Nov. 2005).

Couderc et al., "Electrocardiographic Method for Identifying Drug-induced Repolarization Abnormalities Associated with a Reduction of the Rapidly Activating Delayed Rectifier Potassium Current," Engineering in Medicine and Biology Society 2006, $28^{th}$ Annual Conference of the IEEE (Aug. 2006).

\* cited by examiner

METHODS OF MEASUREMENT OF DRUG INDUCED CHANGES IN CARDIAC ION CHANNEL FUNCTION AND ASSOCIATED APPARATUS

This invention relates to methods and apparatus for measurement of drug induced changes in cardiac ion channel function, and in particular non-invasive methods and apparatus using the Electrocardiogram.

Before being granted a license to market, novel pharmaceutical compounds undergo rigorous cardiac safety testing to ensure they do not predispose the patient to fatal cardiac arrhythmias. Most frequently compounds that impair function of the slow and fast potassium delayed rectifier channels (IKs and IKr), Sodium sustained channel (INasus), calcium sodium calcium pump channel (INaCa), transient outward potassium channel (Ito) and slow calcium current ICaL, are responsible for the cardiac repolarisation abnormalities which leads to these rhythm disturbances. The initial preclinical cardiac safety tests are performed either on in-vivo animal models or on in-vitro animal cardiac cells to assess the various channels function. These methods have proved unreliable because of species differences and variable laboratory conditions. Clinical safety studies use the ECG QT interval prolongation and T wave morphological changes as surrogate markers of drug induced impairment of potassium channel activity. This method has proved insensitive and unsatisfactory also and the pharmaceutical industry seeks a non-invasive, sensitive method to assess the effects of new drugs on the potassium channels in man. This patent seeks to solve the ECG inversion problem by using the ECG to deduce information on the cardiac ion channels.

A myocardial cellular action potential is the cell membrane microvoltage discharge profile with respect to time which occurs when the resting voltage rises above a certain threshold. Under normal conditions pacemakers within the heart induce suprathresholds in nearby cardiac cells which then propagate a charge and voltage outwards from the endocardial (inside) surface of the myocardium through the middle or M cell layer of the myocardium to the epicardial (outside) of the myocardium. The ECG recorded transversely across viable wedges of the three layers of myocardial tissue can be closely simulated by assuming lumped action potential modelling to represent the sum of action potential effects within the endocardial, M cell and epicardial layers. The lumped action potentials (APs) within these three layers are referred to as EndAP, MAP and EpiAP respectively.

FIG. 1 shows schematically myocardial tissue cavity 100 and its endocardial (inside) surface 110, its middle or M cell layer 120 and its epicardial (outside) 130 surface. Arrows 140 show the direction of repolarisation vectors in myocardial wedge 160. FIG. 1 also shows tracings of the action potentials (APs) 170, 180, 190 for each of the endocardial, M cell and epicardial layers, in each case shown relative to the resting potential (RP).

FIG. 2 shows that the timing end of the EpiAP 190 corresponds with the peak of the transverse viable wedge ECG upright T wave 200 and that the three AP durations 170, 180, 190 end in following timing sequence: EpiAP, EndAP and MAP. It can be further shown that the timing of the end of the EndAP corresponds with the peak of the inverted T wave of a wedge ECG and, in this case, the three AP durations end in following timing sequence: EndAP, EpiAP and MAP. It has been found that the ECG T wave measured across a given axis of myocardium can be reconstructed by addition of the instantaneous voltages of (MAPD-EpiAPD)+0.7.(EndAPD-MAPD). The 0.7 is a weighting coefficient used in the work by Yan and Antzelevitch (Yan and Antzelevitch. Cellular Basis for normal T wave and the Electrocardiographic manifestation of the Long QT syndrome. Circulation: 1998 Vol (98). 1928-1936, incorporated herein by reference).

This method of reconstructing an ECG T wave is founded on the physio-anatomical diffusion principle that electrical propagation between cells from endocardium to epicardium traversing across a wedge of the ventricular wall, will generate current dipoles between each pair of adjacent myocardial cells. The magnitude of the intercellular dipole sources is given by the instantaneous potential difference between their APs, and therefore the total instantaneous potential measured at the epicardium, will be a function of the instantaneous sum of these dipole vectors and the position on the epicardium from which they are measured. The instantaneous epicardial potential ECG measured transversely across a human simulated wedge of myocardium can be accurately modelled by computer simulation of a matrix of human cellular cardiac action potentials within the endocardial, M cell and epicardial myocardial layers within that myocardial wedge.

An in vivo ECG recorded transversely across such a viable wedge of myocardium can be measured on the myocardial epicardial surface and is manifested on the ECG of a body surface. Biophysical electrical transmission characteristics of the individual change the morphology but not the temporal duration of the ECG recorded on body surface compared to the epicardial ECG. The epicardial ECGs thus undergo a form of zero-phase filtering. Time consuming and expensive computer tomographic X-Rays have been used to gain information on distances and characteristics of these biophysical transmission factors in order to inversely calculate the epicardial ECG from the body surface ECG of an individual (Y Rudy. Modelling and imaging cardiac repolarisation abnormalities. Journal of Internal Medicine: 2006. Vol (259). 91-106). The body surface ECG is also affected by distant electrical potential field effects from other regions of the myocardium undergoing depolarisation or repolarisation.

Although methods exist which can obtain an epicardial ECG from the body surface ECG, there is as yet no proven method to further inversely derive the instantaneous lumped EpiAP, EndAP and MAP from it. Nor are there any non invasive means to use these APs to estimate the transmural dispersion of repolarisation, AP triangulation of repolarisation nor estimate the myocardial cellular ionic channel conductance within the myocardial layers.

This invention seeks to provide a method to solve this inverse problem using non-invasive recordings made on a human subject by a novel body surface bipolar ECG electrode configuration whilst testing a new pharmaceutical compound. It is envisaged that this invention will not require the use of computer tomographic radiology and that the invention will be incorporated in an apparatus which will enable detection of changes from the baseline in important cardiac cell ionic channel parameters the index of transmural dispersion of repolarisation and the AP triangulation of repolarisation within the transmural layers In a first aspect of the invention there is provided a non-invasive method of measurement of drug induced changes in cardiac ion channel and electrical function said method comprising:

Obtaining a baseline electrocardiogram recorded on the body surface of a person to whom the drug under test has not been administered;

Using a mathematical transformation or convolution of said baseline electrocardiogram and of a typical epicardial electrocardiogram, in order to obtain a filter function representative of biophysical electrical transmission characteristics between epicardial tissue and body surface, said filter function effectively modifying the typical epicardial electrocardiogram to become a body surface electrocardiogram;

Obtaining a second electrocardiogram recorded on the body surface of an individual to whom the drug under test has been administered;

Applying said filter function on a mathematical transformation or convolution of said second electrocardiogram in order to obtain an electrocardiogram representative of a myocardial wedge simulated epicardial electrocardiogram of a person to whom the drug under test has been administered;

Using said representative epicardial electrocardiogram to measure any drug induced changes in cardiac ionic channel and electrical function as a result of said drug under test.

While it is known to use constructed "filters" (a filter in the sense of systematic application of various constructed mathematical algorithms to a signals in the time frequency domain) applied to the body surface ECG to try and reproduce the epicardial ECG, it is not known to use a constructed simulation of epicardial ECG and measured body surface ECG to estimate the system function of the filter, effectively treating the filter as an unknown as in a "black box".

Said typical epicardial electrocardiogram may have been simulated from an in-silico wedge of myocardium.

Said electrocardiograms obtained from the body surface may be obtained from an array of electrodes arranged on the body surface such that they can acquire data from multiples of orthogonally bisecting electrodes. Said electrodes are preferably bipolar electrodes. The distance between each bipolar electrode pole may lie between 0.5 to 3 cm. Each of said multiples of orthogonally bisecting electrodes may be arranged to simultaneously measure the orthogonal (perpendicular) surface vectors such that the instantaneous amplitude of the potential vector along an axis from an electrical source perpendicular to the skin surface can be obtained from the vector cross product of the instantaneous potential vector amplitudes measured along orthogonal surface bipolar electrodes. Preferably, said array of bipolar electrodes are placed over the cardiac apex for the purposes of this application, but in different applications multiple arrays could be applied over the torso (or scalp) surface in order to measure the potential vectors from various electrical sources within the myocardium (or brain) perpendicular to the skin surface In a main embodiment only the T-wave portion of each of the electrocardiogram signals is used.

Said filter function is may be a single transfer function representing the biophysical electrical transmission characteristics between epicardial tissue and body surface. Said filter function may be obtained from Fourier or z transforms of said baseline electrocardiogram and said typical epicardial electrocardiogram, and therefore may itself be represented by a single transfer function in the spectral or z domain.

Each of said electrocardiograms obtained from the body surface may be pre-processed by the following method:

Artefact and ectopic beats are edited out of the signal;

The electrocardiogram's QRST complexes can be ensemble aggregated using the peak R wave as a fiducial point, the median value at each time instant being used to construct a denoised electrocardiogram, or alternatively each QRST complex can be individually analysed;

The QRST complex undergoes further filtering with a zero-phase low pass filter;

The end time point of the T wave is determined; and

The T-wave is isolated over a time period taken from the end time point of the T wave.

Said representative epicardial electrocardiogram may be used to measure any drug induced changes in cardiac ion channel function as a result of said drug under test by reverse engineering from the time of the end of the T wave of said epicardial electrocardiogram, the ionic channel conductances which are active during the time of the latter part of the T-wave. This may be achieved by considering a time period between the time of the end of the T wave of said epicardial electrocardiogram and another earlier time during the same T-wave where it can also be assumed that lumped action potentials for the epicardial and endocardial layers are substantially at resting potential and then calculating the ionic channel conductances for the M cell layer over this time period. Said time period may be between a first time at the end of the T wave and a second time at the time of the peak negative or positive T wave. This second time may lie between where the T-wave is at 50% of its peak value and where the T-wave is at 1% of its peak value or in the range between where the T-wave is at 35% of its peak value and where the T-wave is at 10% of its peak value. Preferably the lumped epicardial and endocardial action potentials are close to resting potential at the chosen second time.

Said calculated values of said ion channel conductances active during the tail end of the lumped M cell layer action potential can be used to calculate tail end lumped action potentials within the endocardial and epicardial layers of a person after administration of the drug under test. This may be done by substituting said conductance values back into a human computer model. The resultant new post drug lumped action potential endocardial layer action potential (EndAP), epicardial layer action potential (EpiAP), and M cell layer action potential (MAP) values may be used to calculate post drug transmural dispersion of repolarisation values. These can be measured simply as the time difference between the end time points between the longest lumped action potential (in this model the lumped M cell layer) and the shortest lumped action potential layer. Action potential Triangulation can also be measured for each lumped action potential calculated as the time difference between the action potential duration at 30% repolarization, known as AP(30), and the action potential duration at 90% repolarization, known as AP(90). The skilled person familiar with electrophysiological terminology and techniques would understand the concept of AP Triangulation.

In a second aspect of the invention there is provided apparatus for carrying out any of the methods described in the previous and forgoing paragraphs in relation to the first and fourth aspects of the invention.

In a third aspect of the invention there is provide an apparatus for obtaining an electrocardiogram (ECG) or electroencephalogram (EEG) from the body surface, said apparatus comprising an array of electrodes arranged on the body surface so as to comprise multiples of orthogonally bisecting electrodes, such that they can acquire instantaneous potential difference data from said body surface.

Said electrodes are preferably bipolar electrodes.

Said instantaneous measurement of potential difference data may be taken along the orthogonally bisecting surface electrodes (that is X,Y vectors) to allow instantaneous calculation of the vector perpendicular to the body surface (the z-vector). Each of said multiples of orthogonally bisecting electrodes may be arranged to simultaneously measure the orthogonal (perpendicular) surface vectors such that the instantaneous amplitude of the potential vector along a perpendicular axis from the cardiac electrical source to the skin surface can be obtained from the vector cross product of the instantaneous potential vector amplitudes measured along the perpendicular axes of these orthogonal surface bipolar electrodes. By calculating the instantaneous potential vector from the source perpendicular to the skin surface and measuring the instantaneous potential at an electrode placed at the bisection of the two orthogonal electrodes it is possible to calculate the instantaneous cardiac source potential. The transverse spatial resolution of the potential vector measured from the source perpendicularly to the skin surface will be proportionate to the length of the surface bipolar electrode axes. The smaller the axes the higher the transverse resolution. Said apparatus may further comprise computing means for computing said vectors, or alternatively said apparatus may be designed to be used in conjunction with a conventional computer.

Preferably, said array of bipolar electrodes are designed to be placed over the cardiac apex for the purposes of detecting changes in ion channel function following drugs. The EEG application of bipolar electrode configuration has no preference for the position of array placement.

The distance between each bipolar electrode pole may lie between 0.5 and 3 cm.

In a fourth aspect of the invention there is provided a method of generating lumped action potentials of a person from an epicardial electrocardiogram comprising:
    considering a time period between the time of the end of the T wave of said epicardial electrocardiogram and another earlier time during the same T-wave where it can also be assumed that lumped action potentials for the epicardial and endocardial layers are substantially at resting potential and then calculating the ionic channel conductances over this time period; and
    Substituting said conductance values back into a human computer model to generate lumped action potentials for the endocardial and epicardial layers of a person.

Said time period may be between a first time at the end of the T wave of said epicardial electrocardiogram and a second time where the inverted or upright T-wave peaks. Alternatively said second time may lie between where the T-wave is at 50% of its peak value and where the T-wave is at 1% of its peak value, or even between where the T-wave is at 35% of its peak value and where the T-wave is at 10% of its peak value Preferably this second time occurs at a time when the lumped epicardial and endocardial action potentials are close to or at the RP. Said method may further comprise obtaining the rate of change of voltage of epicardial electrocardiogram during said time period, and from this obtaining a value of the sum of all ionic currents, said ionic channel conductances being calculated from said value of the sum of all ionic currents.

Said lumped action potentials of a person may be used to calculate transmural dispersion of repolarisation values of a person. This may be measured simply as the time difference between the end time points between the longest lumped action potential and the shortest lumped action potential. AP Triangulation may be measured as AP(30) minus AP(90).

In a fifth aspect of the invention there is provided apparatus for the non-invasive measurement of drug induced changes in cardiac function, said apparatus comprising:
    Input means for the input of a baseline electrocardiogram recorded on the body surface of a person to whom the drug under test has not been administered, a typical epicardial electrocardiogram and a second electrocardiogram recorded on the body surface of an individual to whom the drug under test has been administered;
    Means for comparing said surface baseline electrocardiogram to a typical epicardial electrocardiogram, in order to obtain a filter function representative of biophysical electrical transmission characteristics between epicardial tissue and body surface, said filter function effectively modifying the epicardial electrocardiogram to become a body surface electrocardiogram;
    Means for applying said filter function on said second electrocardiogram in order to obtain an electrocardiogram representative of an epicardial electrocardiogram of a person to whom the drug under test has been administered; and
    Means for using said representative epicardial electrocardiogram to measure any drug induced changes in cardiac ionic and electrical function as a result of said drug under test.

Said input means may include means for the obtaining of at least one of said baseline electrocardiogram recorded on the body surface of a person to whom the drug under test has not been administered, said typical epicardial electrocardiogram and said second electrocardiogram recorded on the body surface of an individual to whom the drug under test has been administered. In the case of obtaining said first and second body surface electrocardiograms, said apparatus may comprise the apparatus of the second aspect of the invention.

In a main embodiment said apparatus is operable such that only the T-wave portion of each of the electrocardiogram signals is used.

Said means for comparing may be operable to obtain a filter function which is ideally a single transfer function representing the biophysical electrical transmission characteristics between epicardial tissue and body surface. Said apparatus may be operable such that said filter function is obtained from Fourier or z transforms of said baseline electrocardiogram and said typical epicardial electrocardiogram, and therefore may itself be represented by a single transfer function in the spectral or z domain.

Said apparatus may further comprise a microprocessor, said microprocessor being arranged to pre-process each of said electrocardiograms obtained from the body surface by the following method:
    Artefact and ectopic beats are edited out of the signal;
    The electrocardiogram's QRST complexes can be ensemble aggregated using the peak R wave as a fiducial point, the median value at each time instant being used to construct a denoised electrocardiogram, or alternatively each QRST complex can be individually analysed;
    The QRST complex undergoes further filtering with a zero-phase low pass filter;
    The end time point of the T wave is determined; and
    The T-wave is isolated over a time period taken from the end time point of the T wave.

Said apparatus may further comprise a analogue to digital converter for pre-processing the input signal.

Said apparatus may be operable such that said representative epicardial electrocardiogram is used to measure any drug induced changes in cardiac ion channel function as a result of said drug under test by reverse engineering from the time of the end of the T wave of said epicardial electrocardiogram, the ionic channel conductances which are active during the time of the latter part of the T-wave. The apparatus may achieve this by being arranged to consider a time period between the time of the end of the T wave of said epicardial electrocardiogram and another earlier time during the same T-wave where it can also be assumed that lumped action potentials for the epicardial and endocardial layers are substantially at resting potential and then calculating the ionic channel conductances over this time period.

Said time period may be between a first time at the end of the T wave and a second time at the time of the peak negative or positive T wave This second time may lie between where the T-wave is at 50% of its peak value and where the T-wave is at 1% of its peak value or in the range between where the T-wave is at 35% of its peak value and where the T-wave is at 10% of its peak value. Preferably, the lumped epicardial and endocardial action potentials are close to resting potential at the chosen second time.

Said apparatus may be further arranged to use said calculated values of said ion channel conductances active during the tail end of the lumped M cell layer to calculate tail end lumped action potentials within the endocardial and epicardial layers of a person after administration of the drug under test. The apparatus may be arranged to do this by substituting said conductance values back into a human computer model, which may or may not form part of the apparatus itself. The apparatus may be further arranged to use the resultant new post drug lumped action potential EndAP, EpiAP and MAP values to calculate post drug transmural dispersion of repolarisation values. These can be measured simply as the time difference between the end time points between the longest lumped action potential (in this model the lumped M cell layer) and the shortest lumped action potential layer.

BRIEF DESCRIPTION OF THE DRAWINGS

Embodiments of the invention will now be described, by way of example only, by reference to the accompanying drawings, in which.

DETAILED DESCRIPTION OF THE EMBODIMENTS

In the following embodiment, electrocardiogram (ECG) recordings will be obtained (non-invasively) from a human subject after given time periods following the administration of a placebo. These will be baseline recordings. Following administration of a compound under investigation given at the same time of day as the placebo but on a separate day, further recordings will be made after the same given time periods.

The baseline and post compound administration bipolar ECG recordings may be taken as follows: Under supine and tranquil conditions several minutes of high resolution recordings of the instantaneous electrical cardiac potential will be made by an analogue to digital recorder from an array of bipolar electrodes arranged in multiples of orthogonally bisecting bipolar electrodes (It is preferable but not essential to use bipolar electrodes). The distance between each bipolar electrode pole may be between 0.5 and 3 cm. The bipolar electrodes are used to simultaneously measure the potential vectors directed from an electrical source (brain or myocardium) orthogonally (perpendicular) to the point of bisection of the measuring bipolar electrodes at the skin surface. Such a bipolar electrode arrangement records vector potentials along axes which near perpendicularly traverse the myocardial wall and are perpendicular to the measuring bipolar electrodes at the skin surface. The lateral resolution of the measured vector potential being proportional to the length of one of the bipolar electrode axes. The smaller the electrode length the higher the resolution. This helps address the aforementioned problem in body surface ECGs, in that they are affected by distant electrical potential field effects from other regions of the myocardium undergoing depolarisation or repolarisation.

Figure 1:
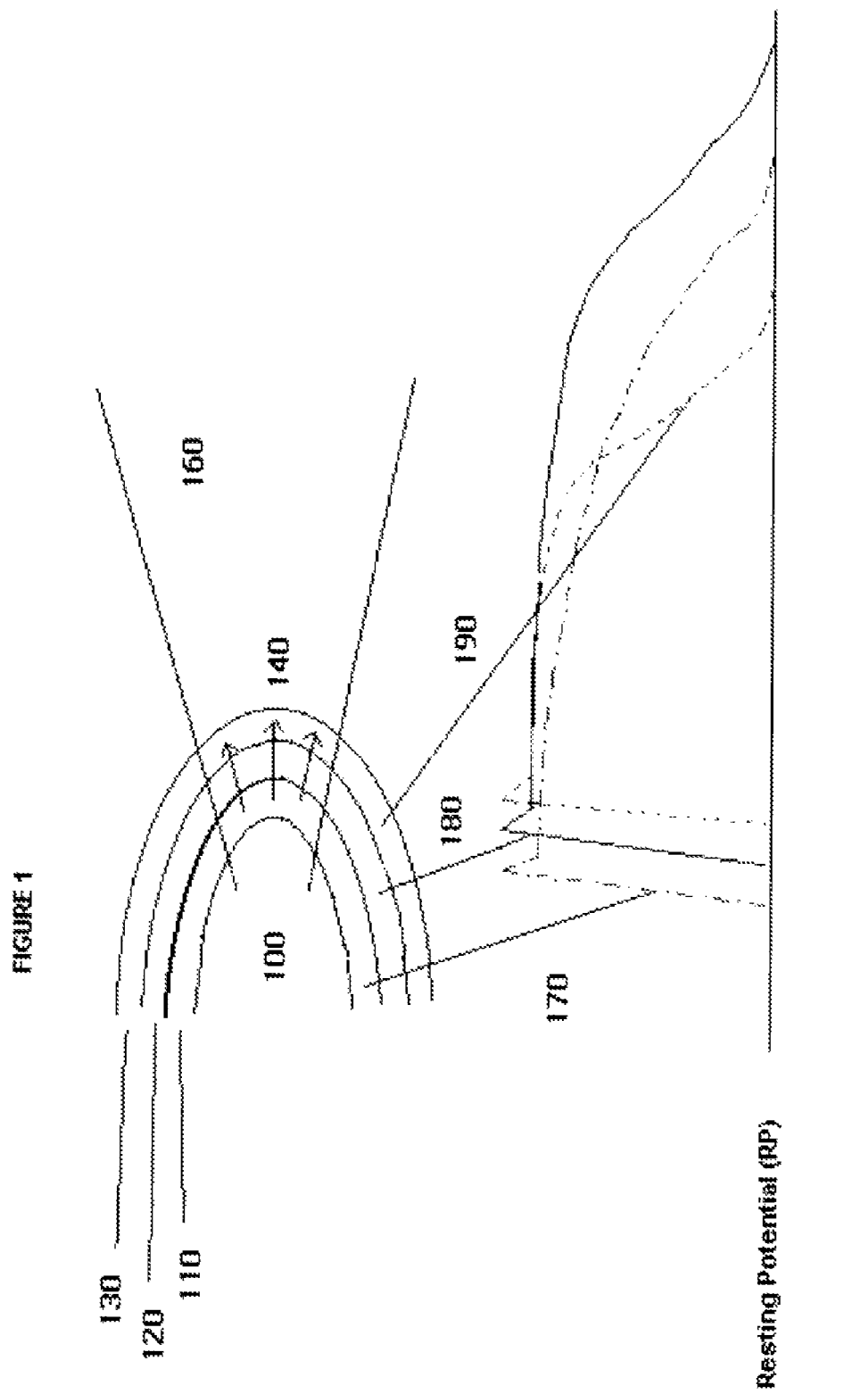
FIG. 1 shows schematically myocardial tissue and Action Potential traces for each myocardial layer.
Figure 2:
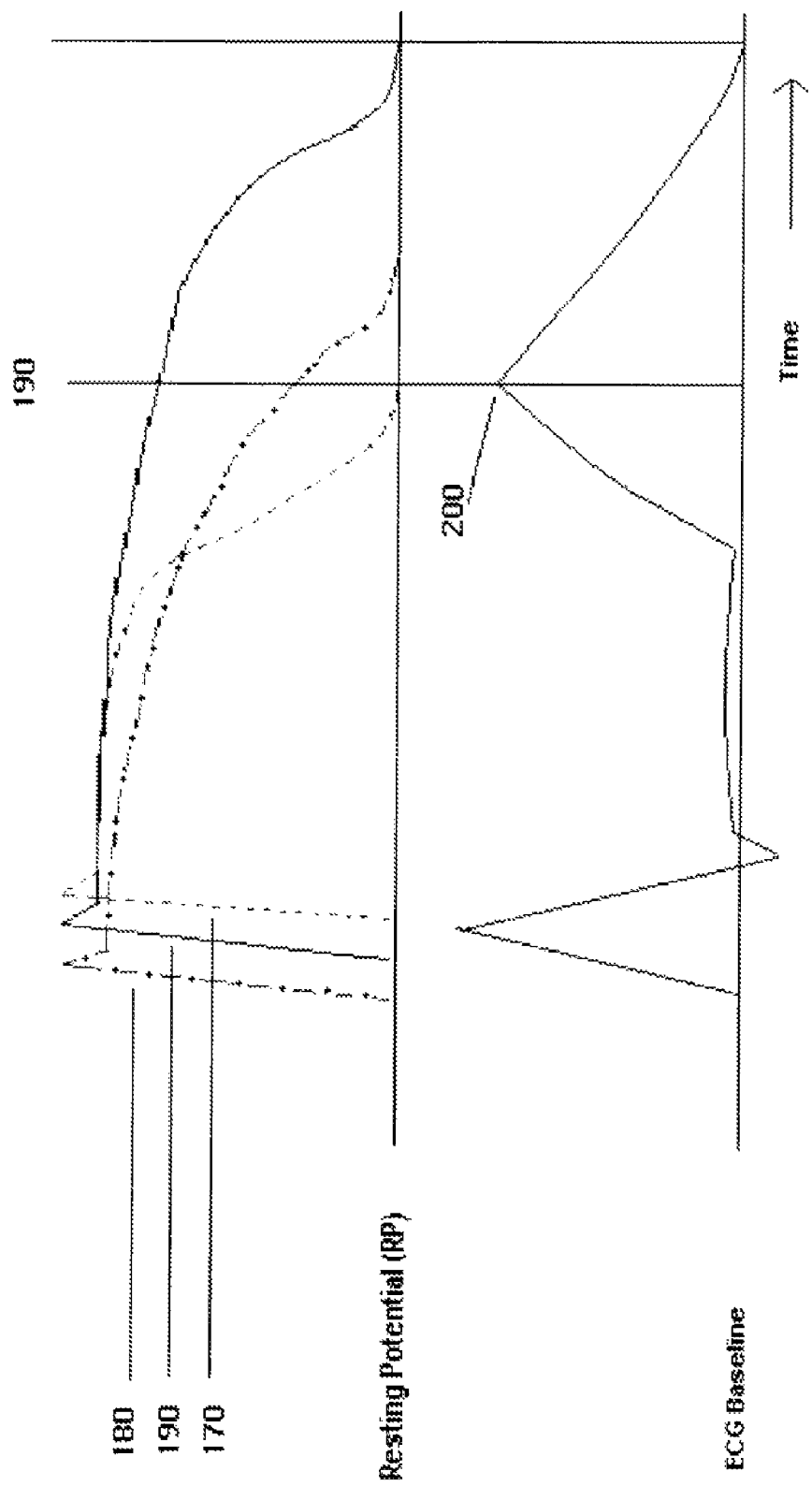
FIG. 2 shows Action Potential traces for each myocardial layer compared over time against the electrocardiogram.
Figure 3:
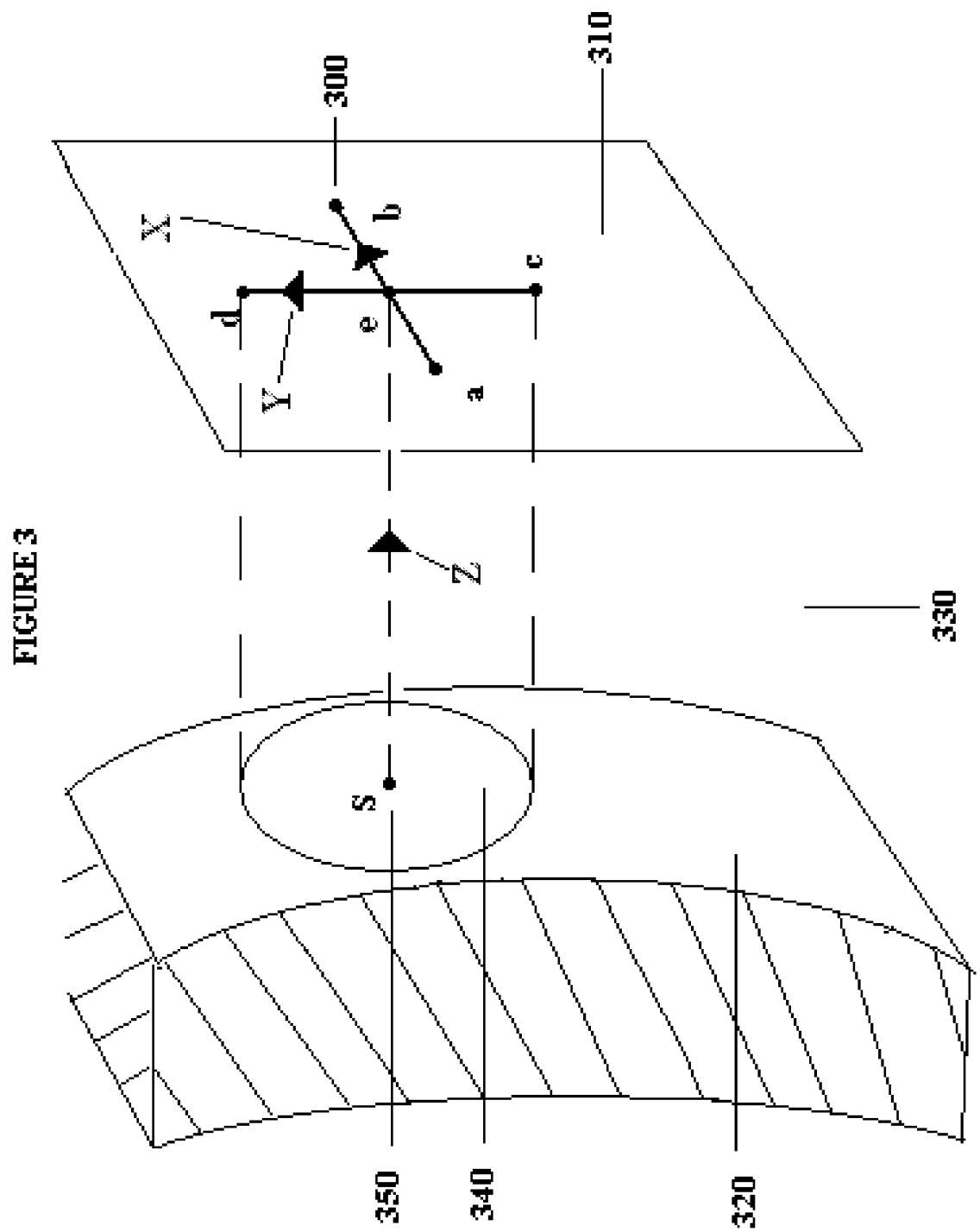
FIG. 3 shows a single unit bipolar electrode arrangement according to an embodiment of the invention, and equivalent vector diagrams.

FIG. 3 shows such an arrangement showing, for clarity, only a single unit of two orthogonal bipolar electrodes 300 on skin surface 310. The single unit 300 comprises a first bipolar electrode pair at a and b, and a second bipolar electrode pair at c and d. There is a further electrode at e, the point of bisection of the two bipolar electrodes.

Also shown is the heart 320 with interstitium 330 therebetween. An electrical source (S) 350 generates the potential vector perpendicular to the bipolar configuration at the skin surface. The X potential vector is measured between electrodes a-b, the Y potential vector is measured between electrodes c-d. The instantaneous Z potential vector generating the instantaneous X and Y vectors at the skin surface can be obtained from the cross product of the X and Y vectors.

Such an arrangement may also be used on, and multiples of such an arrangement may be applied to, the scalp in order to obtain increased 3 dimensional resolution of the EEG (Electroencephalograph), and allow increased resolution of the brain activity in the depth of cerebral cortex over the point of bipolar electrode bisection.

A circle 340 depicts the spatial resolution of the Z vector. This lateral spatial resolution is proportional to the length of the axes of the measuring bipolar electrode.

The vector cross product of the instantaneous potential vector amplitudes along the orthogonal surface bipolar electrodes can then be used to yield the instantaneous amplitude of the potential vector along a perpendicular axis to the skin surface bipolar electrodes (similar application exists for the EEG). Measurement of the instantaneous potential at electrode e plus the instantaneous value of the Z vector will allow calculation of the instantaneous source potential. Therefore when such a multiple formation of bipolar electrodes are placed over the cardiac apex the calculated vector Z will transverse the apex myocardial wall and be close to the long axis of the left ventricle. For the purposes of this invention an echocardiogram may be used to assess the optimum electrode position over the ventricular apex. The vector recordings along the axis perpendicular to such apically positioned bipolar electrodes will be equivalent to making ECG recordings transversely across a wedge of viable apical myocardium.

This electrode design may also be applied to the scalp when making EEG (electroencephalographic recordings) to measure brain action potentials perpendicular to the skin surface, to increase the 3 dimensional resolution.

While there are in existence commercial jackets comprising arrays of uniformly arranged electrodes, these are used to measure the instantaneous body potentials at different surface points to allow the construction of a surface potential map much like the pressure isobars on a weather map. They do not wire 5 adjacent electrodes together though to allow the instantaneous measurement of voltage differences (potentials) along the bisecting orthogonal surface electrodes (that is X,Y vectors) to allow instantaneous calculation of the Z vector (that vector perpendicular to the surface). Nor do they allow calculation of the instantaneous electrical source potential.

Figure 4:
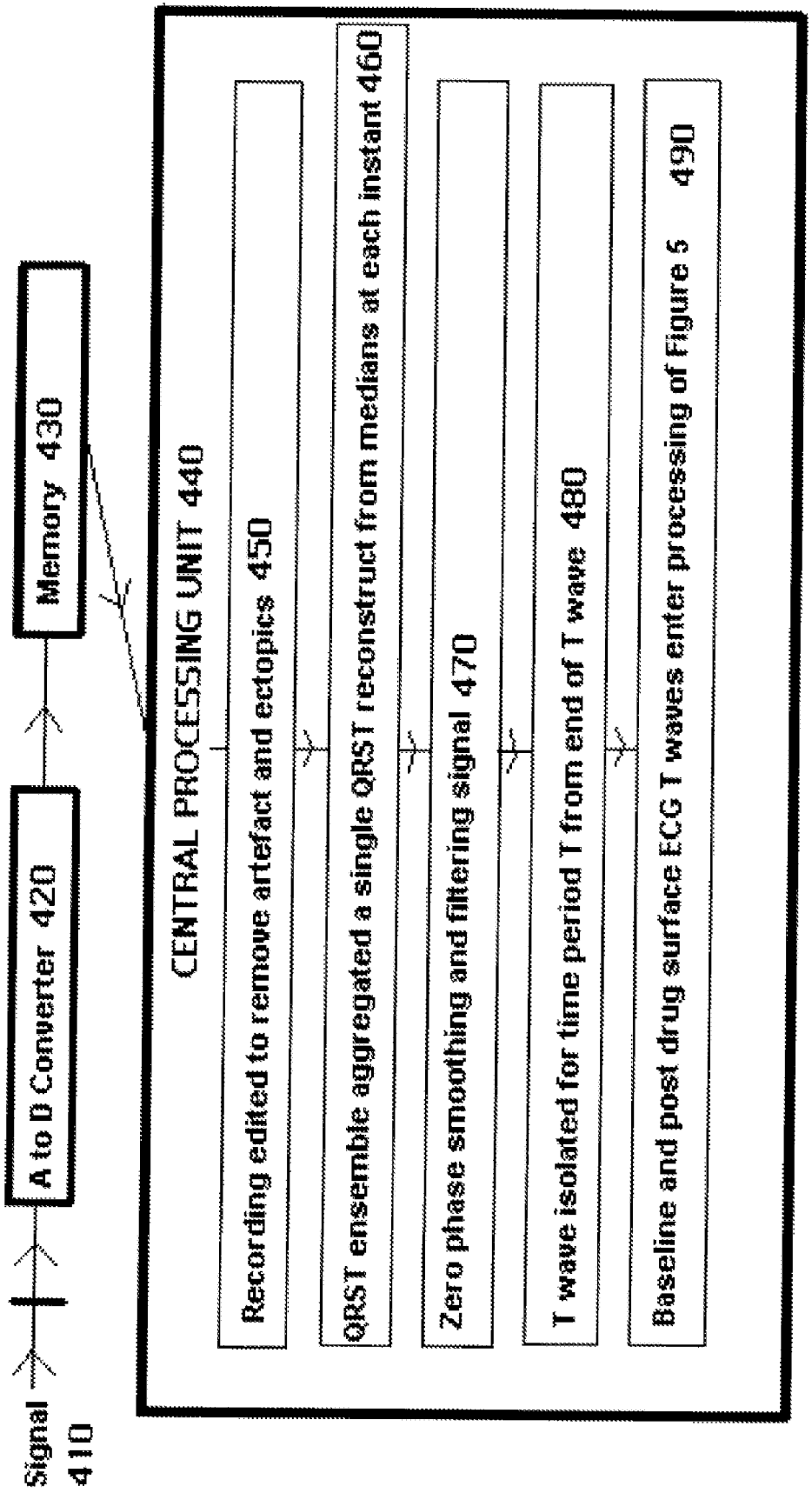
FIG. 4 is a diagram of the pre-processing system for pre-processing the measured electrocardiographs.

FIG. 4 is a diagram of the pre-processing system for pre-processing the measured electrocardiographs. It shows a signal input 410, Analogue to Digital converter 420, memory 430 and central processing unit (CPU) 440. The ECG recordings will be downloaded into a digital processing unit and may be stored to enable off-line processing of data. The stored recordings will then undergo an algorithm, the steps of which a shown in the CPU 440 as a flow diagram:

1. ECG recordings are automatically edited to exclude artefact and ectopic beats 450.
2. The QRST complexes (The QRST complex is the ECG wave complex sited temporally between the P and T waves which represents the electrical potential generated by myocardial cells during the depolarisation phase) will be ensemble aggregated using the peak R wave as a fiducial point and the median value at each time instant will be used to construct a denoised ECG 460. Alternatively a sequence of individual QRST complexes will be analysed over an unspecified time period and the lumped action potentials calculated for each sequential QRST complex. This will allow calculation of the action potential duration variability
3. The QRST complex and will undergo further filtering with a zero-phase low pass filter 470.
4. The end time point of the T wave will be determined 480. This may be done using any of the methods disclosed in GB0208115.6 and PCT/GB2003/004436, the contents of both of which are hereby incorporated by reference.
5. The T will be isolated over a time period taken from the end time point of the T wave 490.

The baseline serum concentration of sodium and potassium in the individual under investigation can be obtained (that is the serum concentration before administration of the compound under investigation). From this a baseline computer simulated myocardial wedge section human ECG T wave may be generated at this potassium and sodium concentration. The end time point of the T wave can also be determined again using one of the methods disclosed in GB0208115.6 and PCT/GB2003/004436 and the T wave then isolated over the same time period as step 5 above, from the end time point of the simulated T wave.

Figure 5:
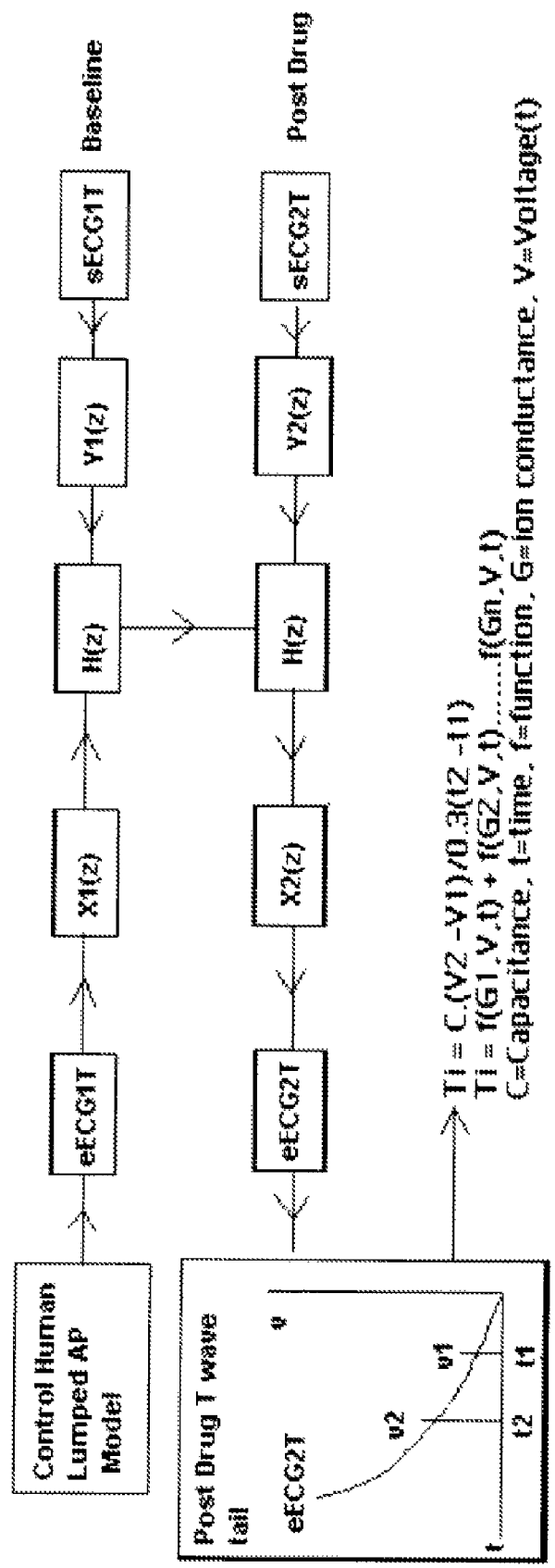
FIG. 5 is a flow diagram showing how, firstly, a post compound epicardial ECG T-wave can be obtained according to one embodiment of the invention, and secondly, how this is used to obtain ionic conductance values according to a further embodiment of the invention.

FIG. 5 is a flow diagram showing how, firstly, a baseline surface ECG T wave and the epicardial ECG T wave simulated from a myocardial wedge section obtain the filter transfer function. Secondly, how the post compound body surface ECG T wave obtains the post compound epicardial ECG T-wave and thirdly, how this is used to obtain the ionic conductance values for the lumped M cell layer.

If the z transform of the simulated epicardial ECG T wave (eECG1T) equals $X1(z)$ and the z transform of the baseline surface ventricular apex ECG T wave (sECG1T) equals signal $Y1(z)$, then the transfer function representing the biophysical transmission filter system $H(z)$ is:

$$H(z)=Y1(z)/X1(z).$$

This filter $H(z)$ can then be applied to the z transformed post administration compound ventricular apex surface ECG T wave (sECG2T), $Y2(z)$ to obtain the post compound z transformed epicardial ECG T wave (eECG2T) signal, $X2(z)$, that is:

$$X2(z)=Y2(z)/H(z)=Y2(z)\cdot X1(z)/Y1(z).$$

A transformation of $X2(z)$ to $X2(t)$ can then be performed to convert the T wave into one described as a function of time (t).

As previously discussed, it can be shown that the post compound eECG2T instantaneous voltages $V(t)$ will be equal to the addition of the instantaneous voltages generated by the three layers myocardium (MAP-EpiAP)+0.7(EndAP-MAP). It was also discussed that, in upright T waves or inverted T waves, the end points (that is the time point at which they return to their iso-electric resting potential RP) of the EndAP or EpiAP occur at approximately the time of the respective positive or negative peaks of their respective T waves. It is known that the MAP returns to the RP at a later time than EndAP and EpiAP return to the RP. The RP is assumed to be that RP at which the baseline eECG1T was modelled, and is therefore known.

Consequently, for a time period between the end time point of MAP and the time at which the T wave is arbitrarily 25% of the peak T wave, it can be safely assumed that the EpiAP and EndAP will be at RP and the tail of eECG2T wave will be generated only by the MAP. During this time period the rate of change of eECG2T with respect to time (dV/dt) will be equal to d((MAP−EpiAP)+0.7(EndAP−MAP))/dt which, since EpiAP and EndAP are constant, simply equals:

$$0.3(dMAP/dt).$$

Going in a forward direction from left to right along the MAP curve, it is known that the rate of change of voltage dV/dt of an AP of the membrane within the lumped MAP layer is equal to the product of (−1/C) (C is membrane capacitance which is known for a human cardiac cell) and the sum of all ionic currents (Ti).

In recognising that the lumped M cell action potential is responsible for tail end of the epicardial T wave, it is possible to numerically reverse engineer this relationship in a discretised form over time increments t2−t1=inc. Considering the T wave in the reverse direction, from the end time point of the T wave:

$$Ti=C(dV/dt)=C.(MAP(t2)-MAP(t1))/(t2-t1)$$

MAP(t2) and MAP(t1) being the voltages within the MAP at times t2 and t1:

If V2 and V1 are the voltages in the eECG2T at times t2 and t1 and we know that (dV/dt)/0.3=dMAP/dt, in discretised form the above becomes:

$$Ti=C.(V2-V1)/(0.3.(t2-t1))$$

Ti consists of the instantaneous sum of all the individual ion channel currents. Each ion channel current is a product between the ion channel conductances and known functions of time and voltage differences MAP-RP. Therefore at each time incrementation from t1 to t2, the calculated C.(V2−V1)/(0.3.(t2−t1)) will equal the sum of all the separate ionic currents This, in turn will equal the sums of the products of individual ion channel conductances and functions of time and the instantaneous MAP voltage which is related to V(t)= (MAP-EpiAP)+0.7(EndAP-MAP). In matrix form this can be written as MA=K where M is a vector of the different ion channel conductances, A is a matrix containing the instantaneous values for all the known functions of time and voltage and K is the instantaneous value of C.(V2−V1)/(0.3(t2−t1)).

Some of the human ion channel conductance values will not be changed by drugs (significantly) during the latter stages of repolarisation (ie during the terminal downslope of the T wave). There are six conductances which are unknown and either numerical methods using linear algebra or wavelet methods will solve for these conductance values for the time period of the tail end of the T wave. Using the new calculated values of the conductances it is possible to substitute back into the human computer model and generate new post drug lumped action potential EndAP, EpiAP and MAP values and therefore permit calculation of post drug transmural dispersion of repolarisation values which can be measured simply as the time difference between the end time points between the longest lumped action potential (in this model the lumped M cell layer) and the shortest lumped action potential layer. The lumped EndAP, EpiAP and MAP Triangulation indices can be calculated as discussed previously.

Other uses of the above methods can also be envisaged. For example, instability of the AP duration, which is the beat to beat variation in AP duration, is a potent predictor of drug induced proarrhythmia. At any given cycle length a long AP duration manifesting on ECG as a long QT interval is followed is followed by a shorter time interval between the preceding peak T wave and the following Q wave (the T-Q) interval. This then results in a subsequent shorter AP duration ie a shorter ECG Q-T interval that is followed by a longer T-Q interval which is followed by a longer QT etc. The result of this is a beat to beat variation in the QT interval and also possibly more variation in the beat to beat T-T interval. The greater magnitude of effect in the T-T interval variability may make this a potent clinical biomarker of drug induced arrhythmia.

When each QRST complex is individually analysed for the baseline and post drug recordings, (as stated above) the beat to beat variability of the individual peak T wave timings is calculated. This can be accomplished within the processing unit by measuring each sequential T-T interval in milliseconds for the duration of ECG recordings made at baseline and post drug, then subjecting the T-T interval data to the same spectral (Fourier or Wavelet techniques) and time domain analytical techniques as used when calculating beat to beat Heart Rate Variability for R-R wave data. The methods of calculating heart rate variability are fully explained by Kobayashi H et al: "Heart Rate variability; an index for monitoring and analyzing human autonomic activity" Applied Human Science. 1999 March; 18(2):53-59.

Summarising the above, the disclosed methods and apparatus enable the calculation of a simple transfer function filter which converts simulated epicardial ECG template into a known surface ECG, and from which any drug induced changes in the surface ECG can be mapped back to give relative changes on the post drug epicardial ECG. This in turn can be relatively mapped back into changes in the lumped layer action-potential model which constructed the baseline simulated epicardial ECG. Because it is known that the downslope of the T wave is generated largely by the end of the M layer action potential, we can use relative changes in the post drug epicardial ECG T wave to derive relative changes in the models lumped M layer action potential and mathematically reverse engineer the conductance values for the ionic channels making up the end of the M layer action potential. The ionic channel conductances can then be used to calculate the post drug lumped EpiAP and EndAPs The above methods and apparatuses are for illustration only, and various modifications can be envisaged without departing from the spirit and scope of the invention.

What is claimed is:

1. A non-invasive method of measurement of drug induced changes in cardiac ion channel and electrical function, said method comprising:
    obtaining a baseline electrocardiogram recorded on a body surface of a person to whom a drug under test has not been administered;
    using a mathematical transformation or convolution of said baseline electrocardiogram and of a typical epicardial electrocardiogram, in order to obtain a filter function representative of biophysical electrical transmission characteristics between epicardial tissue and body surface, said filter function effectively modifying the typical epicardial electrocardiogram to become a body surface electrocardiogram;
    obtaining a second electrocardiogram recorded on the body surface of said person to whom the drug under test has been administered;
    applying said filter function on a mathematical transformation or convolution of said second electrocardiogram in order to obtain a third electrocardiogram representative of a myocardial wedge simulated epicardial electrocardiogram of a person to whom the drug under test has been administered; and
    using said third electrocardiogram to measure any drug induced changes in cardiac ionic channel and electrical function as a result of said drug under test based on measurements of a shape of the third electrocardiogram.

2. A method as claimed in claim 1 wherein said electrocardiograms obtained from the body surface are obtained from an array of electrodes arranged on the body surface such that they can acquire data from multiples of orthogonally bisecting electrodes.

3. A method as claimed in claim 2 wherein said electrodes are bipolar electrodes.

4. A method as claimed in claim 2 wherein a distance between each bipolar electrode pole lies between 0.5 to 3 cm.

5. A method as claimed in claim 2 wherein each of said multiples of orthogonally bisecting electrodes is arranged to simultaneously measure the orthogonal surface vectors such that the instantaneous amplitude of a potential vector along an axis from an electrical source perpendicular to the body surface can be obtained from a vector cross product of the instantaneous potential vector amplitudes measured along perpendicular axes of said orthogonally bisecting electrodes.

6. A method as claimed in claim 3 wherein said array of bipolar electrodes are placed over the cardiac apex.

7. A method as claimed in claim 1 wherein only a T-wave portion of each of the electrocardiogram signals is used.

8. A method as claimed in claim 1 wherein said filter function is a single transfer function representing the biophysical electrical transmission characteristics between epicardial tissue and body surface.

9. A method as claimed in claim 8 wherein said filter function is obtained from Fourier or z-transforms of said baseline electrocardiogram and said typical epicardial electrocardiogram.

10. A method as claimed in claim 8 wherein said filter function is represented by a single transfer function in the spectral or z-domain.

11. A method as claimed in claim 1, wherein each of said electrocardiograms obtained from the body surface is preprocessed by one or more of the following method steps:
    editing the signal to remove artefact and ectopic beats;
    preparing a QRST complex for analysis by either:
        aggregating the electrocardiogram's QRST complexes using peak R wave as a fiducial point and using a median value at each time instant to construct a denoised electrocardiogram; or
        selecting an individual QRST complex for analysis;
    filtering the prepared QRST complex using a zero-phase low pass filter;
    determining an end time point of a T-wave; and
    isolating the T-wave over a time period taken from the end time point of the T-wave.

12. A method as claimed in claim 1 wherein said typical epicardial electrocardiogram has been simulated from an in-silico wedge of myocardium.

13. A method as claimed in claim 1 wherein said representative epicardial electrocardiogram is used to measure any drug induced changes in cardiac ion channel function, as a result of said drug under test, by calculating from a time of the end of a T wave of the third electrocardiogram, ionic channel conductances being active during the time of a latter part of the T-wave.

14. A method as claimed in claim 13 comprising the step of considering a time period between the time of the end of the T-wave of the third electrocardiogram and another earlier time during the same T-wave where it can also be assumed that lumped action potentials for the epicardial and endocardial layers are substantially at resting potential and further comprising calculating the ionic channel conductances for an M cell layer over this time period.

15. A method as claimed in claim 14 wherein said time period lies between a first time at the end of the T wave and a second time at the time of the peak negative or positive T wave.

16. A method as claimed in claim 15 wherein said second time lies between where the T-wave is at 50% of its peak value and where the T-wave is at 1% of its peak value.

17. A method as claimed in claim 15 wherein said second time lies in the range between where the T-wave is at 35% of its peak value and where the T-wave is at 10% of its peak value.

18. A method as claimed in claim 15 wherein the lumped epicardial and endocardial action potentials are close to resting potential at the chosen second time.

19. A method as claimed in claim 13 wherein said calculated values of said ion channel conductances active during a tail end of a lumped M cell layer action potential are used to calculate tail end lumped action potentials within the endocardial and epicardial layers of a person after administration of the drug under test.

20. A method as claimed in claim 19 wherein said step of calculating said tail end lumped action potentials is done by substituting said conductance values back into a human computer model.

21. A method as claimed in claim 20 wherein obtained post drug lumped action potential endocardial layer action potential (EndAP), epicardial layer action potential (EpiAP), and M cell layer action potential (MAP) values are used to calculate post drug transmural dispersion of repolarisation values.

22. A method as claimed in claim 21 wherein said transmural dispersion of repolarisation values is measured as a time difference between end time points between a longest lumped action potential and a shortest lumped action potential.

23. A method as claimed in claim 19 wherein an action potential triangulation is measured for each lumped action potential calculated, as the time difference between the action potential duration at 30% repolarization and the action potential duration at 90% repolarization.

24. An apparatus adapted to carry out the method as claimed in claim 1.

* * * * *